US005856359A

United States Patent [19]

Fischer et al.

[11] Patent Number: 5,856,359

[45] Date of Patent: Jan. 5, 1999

[54] THYROXINE/CYCLODEXTRIN COMPLEXES AND PHARMACEUTICAL COMPOSITIONS CONTAINING THE SAME

[75] Inventors: Wilfried Fischer; Daniel Bracher, both of Holzkirchen, Germany

[73] Assignee: Hexal AG, Germany

[21] Appl. No.: 875,366

[22] PCT Filed: Nov. 28, 1996

[86] PCT No.: PCT/EP96/05275

§ 371 Date: Jul. 24, 1997

§ 102(e) Date: Jul. 24, 1997

[87] PCT Pub. No.: WO97/19703

PCT Pub. Date: Jun. 5, 1997

[30] Foreign Application Priority Data

Nov. 29, 1995 [HU] Hungary .............................. P9503407

[51] Int. Cl.[6] ...................... A61K 31/195; A61K 31/715

[52] U.S. Cl. .............................................. 514/567; 514/58

[58] Field of Search ...................................... 514/58, 567

[56] References Cited

U.S. PATENT DOCUMENTS

| | | | |
|---|---|---|---|
| 2,827,452 | 3/1958 | Schlenk et al. | 260/209 |
| 4,834,985 | 5/1989 | Elger et al. | 424/488 |
| 5,126,333 | 6/1992 | Martini et al. | 514/58 |
| 5,134,127 | 7/1992 | Stella et al. | 514/58 |
| 5,206,025 | 4/1993 | Courteille et al. | 424/439 |

OTHER PUBLICATIONS

Szente, Lajos et al., "Spontaneous Opalescence of Aqueous γ–Cyclodextrin Solutions: Complex Formations or Self–Aggregation?", 14 pages, (Unpublished).

Handbook of Pharmaceutical Excipients, published by the American Pharmaceutical Association, pp. 41–42, 1986.

*Primary Examiner*—Raymond Henley, III
*Attorney, Agent, or Firm*—Brooks & Kushman P.C.

[57] ABSTRACT

Thyroxine containing pharmaceutical compositions with improved aqueous solubility, stability and enhanced membrane permeation have been prepared by formulating thyroxine with cyclodextrins. These thyroxine/cyclodextrin complexes can further be transformed into different dosage forms (oral tablets, injectables, transdermal patches, hydrogels, ointments, suppositories etc.) by employing known, common pharmaceutical additives.

16 Claims, No Drawings

THYROXINE/CYCLODEXTRIN COMPLEXES AND PHARMACEUTICAL COMPOSITIONS CONTAINING THE SAME

This is a 371 of PCT/EP96/05275 filed Nov. 28, 1996.

Thyroxine containing pharmaceutical compositions with improved aqueous solubility, stability and enhanced membrane permeation have been prepared by formulating thyroxine with cyclodextrins. These thyroxine/cyclodextrin complexes can further be transformed into different dosage forms (oral tablets, injectables, transdermal patches, hydrogels, ointments, suppositories etc.) by employing known, common pharmaceutical additives.

The present invention relates to complexes of thyroxine and cyclodextrin and pharmaceutical compositions thereof suitable for oral, and parenteral or transdermal administration. In the present invention thyroxine stands for L-thyroxine or D-thyroxine or a pharmaceutical acceptable salt thereof or any racemate thereof.

Deficiency of thyroid activity, whether occurring spontaneously or resulting from surgical removal of thyroid gland, thyroiditis, or decreased function secondary to pituitary degeneration results in clinical hypothyroidism. Whatever the cause, the symptom is treated by replacement therapy using thyreoglobulin or salts of thyroxine, like Levothyroxine-sodium.

Levothyroxine (L-thyroxine) {0-(4-hydroxy-3,5-diiodophenyl)-3,5-diiodotyrosine} is an iodinated aminoacid of the thyroid gland that exerts a stimulating effect on metabolism (Kendall, J. Am. Med. Assoc. 64. 2042. 1915.). Levothyroxine sodium as drug has been used mainly in tablet form with a unit dose of around 0.1 mg per tablet.

Dextrothyroxine (D-throxine) is the D-configuration of the natural occuring thyroid gland hormone and exhibits cholesterol and lipid lowering effects.

Cyclodextrins (CDs) are prepared from starches using CD-glucosyl transferase enzyme. There are three different kinds of CDs, i.e. the α-, β- and γ-CD, which consists of 6, 7 or 8 glucopyranose units connected with –1.4 glucosidic bonds. The three cyclodextrins differ in molecular weight, water-solubility and in cavity-diameter. Accordingly they are able to form inclusion complexes with most of compounds, but the inclusion complexes of the same compound are formed with different kinds of CD having very different properties. There is a possibility to carry out further modifications in the CD molecule with suitable substitutions. For example in case of heptakis-2,6-di-0-methyl-β-CD (DIMEB) two hydroxyl groups of every glucose unit are methylated, while in case of randomly methylated β-CD (RAMEB) the hydroxy groups are substituted randomly by methoxy groups, however the average degree of methylation is around 1,8. The hydroxyalkylation of cyclodextrins also results in improved aqueous solubility as known for hydroxypropylated and hydroxyethylated cyclodextrine derivatives (Szejtli, J. Cyclodextrin Technology, Kluwer Academic Publ. 1988. page 51.).

The solubility of these chemically modified cyclodextrins reaches the value of about 400–500 mg/ml at room temperature and their complex-forming capacity also differs from the unsubstituted CDs.

The interaction of thyroxine with cyclodextrins has not yet been reported. Thyroxine/cyclodextrin inclusion complexes as ingredients of any pharmaceutical formulations have never been previously described in any paper or patent.

The U.S. Pat. No. 4,121,975 (Ullman, E.; Lavine, F. and Joel, E.) deals with the analytical determination of serum thyroxine levels in patients by competitive protein-binding or immunoassay, employing also γ-cyclodextrin for the selective removal of interfering components (mainly blood lipids) present in the blood samples.

There is a lot of literature—both publications and patents—which describes the enhancement of poorly soluble drugs with cyclodextrins and with the concomitant consequences, like improved bioavailability, chemical and/or physical stability of the cyclodextrin complexed drug (Szejtli, J.: Cyclodextrin Technology, Kluwer Academic Publ., Dordrecht, Holland, 1988, p. 186–197). Summarizing the available data it can be stated that in most cases the β-CD is the best complexing agent for hydrophobic, poorly soluble drugs and among the β-cyclodextrins the alkylated (methylated) and the hydroxyalkylated (hydroxypropylated) β-cyclodextrins are the most appropriate ones. Only in a few cases the γ-cyclodextrin showed to be as good as a β-cyclodextrin derivative and in no case it has been published that the chemically non-modified, so-called parent γ-cyclodextrin—at identical cyclodextrin concentration—results in a more than 2.5-fold solubility enhancement as compared with the best solubilizer known, the heptakis-(2,6-di-0-methyl)-β-cyclodextrin (Pitha, J. Life Sci.29.367.1981).

This unexpected experimental finding is the core of the present invention.

It is well-known, that γ-cyclodextrin exhibits the highest aqueous solubility among all parent-cyclodextrins. However, its solutions are physically not stable, because the aqueous solutions of highly purified γ-cyclodextrins tend to become turbid within days at room temperature, even at ⅕ of the saturation concentration. A further unexpected observation is that these γ-cyclodextrin containing aqueous solutions and hydrogels remain clear without formation of any solid crystalline or amorphous precipitate.

The unexpected excellent physical stability of aqueous thyroxine/γ-cyclodextrin solutions in the physiologically acceptable pH-range is the other essential feature of our invention, because only the simultaneous prevalence of these two properties makes it possible to prepare a thyroxine/γ-cyclodextrin containing transdermal patch formulations. High concentrations of drug as well as physical stability of the solution and chemical stability of the dissolved drug are the preconditions for an appropriate transdermal thyroxine patch formulation.

Interaction between L-thyroxine sodium and cyclodextrins in presence of water.

One evidence of the interaction between L-thyroxine and cyclodextrins is that the cyclodextrins increase the aqueous solubility of the thyroxine as shown in Table 1.

TABLE 1

Solubility of L-thyroxine sodium salt in the presence of CDs (mg/ml)

| conc. of CDs (%) | γ-cyclo-dextrin | 2-hydroxy-propylated-β-cyclodextrin | randomly-methylated-β-cyclodextrin | heptakis-2,6-di-O-methyl-β-cyclodextrin | Maltosyl-β-cyclodextrin |
|---|---|---|---|---|---|
| 0 (no CDs) | 2.0 | 2.0 | 2.0 | 2.0 | 2.0 |
| 1.0 | 5.48 | 1.44 | 3.70 | 3.16 | 2.29 |
| 3.0 | 12.10 | 3.10 | 6.15 | 5.50 | 2.48 |

TABLE 1-continued

Solubility of L-thyroxine sodium salt in the presence of CDs (mg/ml)

| conc. of CDs (%) | γ-cyclodextrin | 2-hydroxy-propylated-β-cyclodextrin | randomly-methylated-β-cyclodextrin | heptakis-2,6-di-O-methyl-β-cyclodextrin | Maltosyl-β-cyclodextrin |
|---|---|---|---|---|---|
| 5.0 | 16.90 | 2.90 | 8.36 | 7.00 | 2.32 |
| 7.0 | 26.55 | 2.74 | 9.33 | 7.62 | 2.94 |
| 10.0 | 27.00 | 2.77 | 10.32 | 8.20 | 2.73 |
| 12.0 | 35.10 | 3.05 | 13.30 | 12.13 | 2.80 |
| 15.0 | 44.20 | 3.14 | 16.80 | 14.24 | 2.68 |

As can be concluded from the above data, among the studied unsubstituted cyclodextrins the γ-cyclodextrin was found to improve the aqueous solubility of L-thyroxine sodium most remarkably, thus to have the highest affinity towards the drug. It has unexpectedly been found that among the highly water-soluble β-cyclodextrin derivatives methylated-β-cyclodextrins (both randomly methylated and heptakis 2,6-di-O-methyl-cyclodextrins) appear to be less potent solubilizers of thyroxine, than the chemically non-modified γ-cyclodextrin. It is further demonstrated that 2-hydroxypropylated β-cyclodextrin (HPBCD) and maltosyl-β-cyclodextrin have shown not to be really feasible solubilizing agents for thyroxine, since they did not significantly improve the aqueous solubility of thyroxine even at higher applied concentrations.

It is also important that the parent α-cyclodextrin and β-cyclodextrin had practically no effect on the solubility of thyroxine.

Thyroxine/Cyclodextrin Formulations

Thyroxine can react with the cyclodextrins or their derivatives in aqueous medium. Having attained the required clarity of common aqueous solutions, water can be removed from the reaction mixture by known methods, i.e. by freeze-drying or spray drying. In certain cases, when necessary, only a small amount of a suitable, pharmaceutically acceptable organic solvent or detergent can be used as a third component in the formulations. According to an alternative method, the thyroxine and cyclodextrins can be kneaded in the presence of small amounts of water.

Pharmaceutical Dosage Forms

The thyroxine/γ-cyclodextrin complexes can be used for the preparation of common pharmaceutical dosage forms like tablets, gels, ointments, cremes, injectables, suppositories, patches and plasters.

For the preparation of tablets the complexes are either freeze-dried or spray-dried and mixed with suitable excipients to obtain fast or slow release tablets.

Hydrogels containing the complexes of the present invention can be prepared by using water swellable polymers like polymers of acrylic acid, cellulose derivates, polyvinylpyrrolidone or gelatine.

Additionally, the aqueous solutions according to the invention can obtain stabilizers, antioxidants, or thickeners like pectins, alginates or silicium dioxides. Hydrogel preparations or aqueous solutions of the complexes may be filled in reservoir patches as described in the prior art.

The following examples serve for illustration and do not limit the present invention.

EXAMPLE 1

Preparation of thyroxine/γ-cyclodextrin formulation 20 ml of a 10% aqueous γ-CD solution was intensively stirred at room temperature and to this solution 500 mg of L-thyroxine-Na is added without any solvent. The reaction mixture was further stirred for 12 hours at room temperature with 600 r.p.m. The resulting slightly opalescent solution was then freeze dried yielding 2.28 g of white, nearly amorphous solid that has a thyroxine content of 20.12% by weight.

Redissolution properties of the product according to Example 1: The reconstitution of this lyophilized powder results in a slightly opalescent solution, when 0.1 g of the product is dissolved in 2 ml of distilled water (no solid particles are observed upon standing for two hours).

EXAMPLE 2

Preparation of thyroxine/randomly methylated-β-cyclodextrin formulation 100 mg of L-thyroxine-Na is added to 10 ml of 10% aqueous methylated-β-cyclodextrin solution (average degree of methylation is 1.8 methoxy per glucose unit) and the reaction mixture is stirred for 12 hours at room temperature. The slightly opalescent solution is filtered across a membrane of 0.42 m and the clear filtrate is lyophilized. The resulting white amorphous powder is 1.07 g. The L-thyroxine content of the formulation is 9.25% by weight.

The redissolution properties of the product prepared according to Example 2.

The formulation can be dissolved in water or in physiological buffered saline resulting in a clear, transparent solution.

EXAMPLE 3

Preparation of L-thyroxine/γ-cyclodextrin complex by kneading 6.48 g (0.005 mole) of γ-cyclodextrin is wetted with 10 ml of deionized water and intensively grounded for 5 minutes. 0.799 g (0.001 mole) of L-thyroxine-Na is added to the γ-CD. The mixture is kneaded for 30 minutes at room temperature to obtain a white cream. The creamy material is dried over $P_2O_5$ at room temperature to constant weight.

The dry complex is a white or nearly white powder that has a thyroxine content of 10.6% by weight.

EXAMPLE 4

Preparation of L-thyroxine sodium/cyclodextrin containing hydrogels 8 ml of a 70 mg/ml solution of γ-cyclodextrin was stirred with 142 mg of thyroxine-Na to obtain a clear transparent solution. 150 mg of a water swellable polymer (i.e. Klucel; Hercules Corp. USA) was added. The mixture was ultrasonicated for 10 minutes and stirred for 3 hours to obtain a slight opalescent hydrogel. The stability of the hydrogel according to example 4 was found to be satisfactory over a storage period of two weeks at 25° C. Neither any precipitation in the gel nor decreasing of the content of the solubilized thyroxine in the formulation was detected.

EXAMPLE 5

Preparation of L-thyroxine sodium/methyl-β-cyclodextrin containing hydrogels 10 ml of the 10% aqueous randomly methylated-β-cyclodextrin solution was intensively stirred at 25° C. with 80 mg of L-thyroxine-Na for 4 hours to obtain a clear solution. To this solution 250 mg of Klucel (Hercules Corp. USA) was added and ultrasonicated for 10 minutes. The mixture was further stirred for 5 hours to obtain a transparent or slightly hazy hydrogel.

The gel according to example 5 was found to be stable at 25° C. for two weeks, without precipitation or loss of the dissolved thyroxine content.

EXAMPLE 6

Preparation of aqueous topical gel containing L-thyroxine sodium /γ-cyclodextrin The aqueous gel containing γ-cyclodextrin solubilized thyroxine was prepared by mixing at room temperature 150 mg of Pionier NP37 (polyacrylic acid) with 10 ml of 10% aqueous γ-cyclodextrin solution containing 300 mg solubilized L-thyroxine-Na. The aqueous topically applicable formulation according to example 6 was a transparent, glassy gel. This gel can be stored in closed vials at room temperature for two weeks without significant decrease of the active ingredient or drug precipitation.

EXAMPLE 7

Preparation of transdermal tape with L-thyroxine-Na/methyl-cyclodextrin content 50 ml of 10% aqueous heptakis-2,6-di-O-methyl-β-cyclodextrin solution containing 9.5 mg/ml dissolved L-thyroxine sodium is mixed at 25° C. with 100 g of acrylic acid-2-ethylhexyl-acrylate copolymer and 0.1 g of preservative (sorbic acid) to obtain a clear or slightly opalescent gel that can directly be applied to a polyester foil and dried to give a transdermally applicable tape.

EXAMPLE 8

Preparation of a transdermal therapeutic system containing L-thyroxine-Na/γ-cyclodextrin 500 μl of the formulation of example 6 are filled into a reservoir patch consisting of a release liner, a backing foil, which is heat-sealed to a membrane that is coated with a pressure sensitive adhesive. Alternatively or additionally the reservoir system can have a peripherial adhesive ring.

EXAMPLE 9

Preparation of thyroxine/γ-cyclodextrin containing oral tablets

The lyophilized, water-soluble formulation of thyroxine with γ-cyclodextrin according to Example 1 having 20.1% by weight of L-thyroxine sodium is mixed with common tabletting additives and compressed into tablets of 100 mg mass with an active ingredient content of 0.1 mg per tablet as described below:

| | |
|---|---|
| L-thyroxine/γ-cyclodextrin complex lyophilisate | 0.50 mg |
| Avicel | 52 mg |
| Stearic acid | 15 mg |
| Aerosil R-972 | 12 mg |
| Aerosil 300 | 3 mg |
| Vinylpyrrolidone-vinyl-acetate copolymer | 15 mg |
| Maize starch | 2.5 mg |

The same composition can be prepared by using kneaded L-thyroxine-Na/γ-cyclodextrin formulation according to Example 3.

EXAMPLE 10

Preparation of thyroxine/methyl-β-cyclodextrin containing suppositories

Suppositories of 2 g mass with 0.1 mg active ingredient can be prepared from thyroxine/methyl-β-cyclodextrin lyophilized formulation according to example 2 in a known manner with the following composition:

0.108 g L-thyroxine/methylated β-cyclodextrin according to example 2 was added slowly to 200 g of the previously molten Massa estarinum and 100 suppositories were prepared from the composition. The content uniformity of the cyclodextrin complexed thyroxine in suppositories was found to be improved as a result of the inhibition of the migration of the thyroxine within the suppository base upon storage.

EXAMPLE 11

In vitro membrane permeation studies

The comparison of the membrane permeation of free and—cyclodextrin complexed L-thyroxine-Na from a Pionier NP37 based hydrogel showed that the formulation of the thyroxine with—cyclodextrin results in a significantly improved membrane permeation through a cellulose-acetate membrane (Medicel Intl. Ltd. Dialysis Visking Tubing membrane 13-2"). The study was carried out at 37° C. in buffered media at pH 5.7 and the results of the membrane permeation study are listed in Table 2.

TABLE 2

Membrane permeation of free and γcyclodextrin complexed L-thyroxine-Na from a Pionier NP37 hydrogel according to example 6.

| | dissolved L-thyrocine-Na in outer compartment (g/ml) | |
|---|---|---|
| time (minutes) | Pionier NP37 thyroxine/γ-cyclodextrin complex | Pionier NP37 thyroxine |
| 15 | 3.6 | 0 |
| 30 | 14.8 | 0 |
| 40 | 20.3 | 0 |
| 50 | 22.8 | 0 |
| 60 | 26.5 | 0.7 |
| 80 | 31.8 | 3.0 |
| 100 | 37.6 | 9.1 |
| 120 | 38.9 | 11.0 |
| 210 | 54.8 | 19.1 |
| 240 | 57.3 | 24.7 |

EXAMPLE 12

Physical stability of aqueous topical gel according to example 6

10 ml of the aqueous Pionier NP37-thyroxine/γ-cyclodextrin formulation was stored in sealed polyethylene bags as well as in capped glass vials under normal laboratory conditions (22° C. exposed to day light) for two weeks and the turbidity of the samples was investigated. After two weeks of storage no precipitate formation was visually observed. The total dissolved amount of L-thyroxine-Na was found to remain homogeneously distributed in the hydrogel after two weeks of storage. (The control gels containing the same amount of L-thyroxine-Na without—cyclodextrin were all white, milky suspensions.)

Also it is to be noted that clear aqueous γ-cyclodextrin solutions without any dissolved L-thyroxine-Na content turned to be hazy within three days, then after one week of storage a small amount of white precipitate formation occurred during storage. This phenomenon was not observed in case of L-thyroxine-Na/γ-cyclodextrin containing hydrogels of Klucel or Pionier NP37.

EXAMPLE 13

Solubilization of L-thyroxine free acid form with γ-cyclodextrin

The aqueous solubility of the free acid form of L-thyroxine was found to be in the range of 0.11–0.15 mg/ml. This poor solubility can be affected positively by employing γ-cyclodextrin. The effect of γ-cyclodextrin as to the aqueous solubility of thyroxine acid is shown by the results in the table below:

TABLE 3

Aqueous solubility of thyroxine free acid in the presence of γ-cyclodextrin at 25° C. studied on two parallel experiments.

| Concentration of γ-cyclodextrin (g/100 ml) | solubility of thyroxine free acid in mg/ml 1-st run | 2-nd run |
|---|---|---|
| 0 | 0.110 | 0.150 |
| 5 | 0.400 | 0.379 |
| 10 | 0.646 | 0.652 |
| 12 | 0.765 | 0.800 |
| 15 | 1.02 | 1.00 |
| 20 | 1.39 | 1.44 |

As can be seen from the above data the aqueous solubility of the acid form of thyroxine can be enhanced by about ten-fold using—cyclodextrin in a concentration of 20% by weight.

EXAMPLE 14

Preparation of L-thyroxine free acid/γ-cyclodextrin complex 0.54 g of γ-cyclodextrin and 0.137 g of L-thyroxine free acid were intensively co-grounded in 0.5 ml of 50% (v/v) aqueous ethanol at room temperature for 30 minutes.

The mixture was then allowed to dry at room temperature and sieved to obtain 0.532 g of white powdery solid L-thyroxine/γ-cyclodextrin formulation. The formulation was analyzed for L-thyroxine acid content by UV spectrophotometry and it was found that the complex had 18.7% of weight L-thyroxine acid.

This formulation provides improved wettability and dissolution properties for the entrapped L-thyroxine acid.

We claim:

1. A transdermal composition comprising a solution or hydrogel of γ-cyclodextrin and a thyroxine selected from the group consisting of L-thyroxine, D-thyroxine, a pharmaceutically acceptable salt of L-thyroxine, a pharmaceutically acceptable salt of D-thyroxine, and mixtures thereof.

2. The composition of claim 1 wherein said pharmaceutically acceptable salt is a sodium salt.

3. The composition of claim 1 wherein said thyroxine is a free acid of D-thyroxine or L-thyroxine.

4. The composition of claim 1 wherein the molar ratio of γ-cyclodextrin to thyroxine is from about 25:1 to about 0.5:1.

5. The composition of claim 4 wherein said molar ratio is from about 4:1 to 1:1.

6. The composition of claim 1 wherein said thyroxine comprises L-thyroxine sodium.

7. A process for the preparation of a composition according to claim 1, comprising kneading said γ-cyclodextrin with said thyroxine in the presence of water.

8. The process of claim 7 wherein said water is present in an amount corresponding to the amount of water necessary to solubilize said composition up to twice that amount of water.

9. A pharmaceutically active thyroxine preparation comprising the composition of claim 1.

10. The pharmaceutically active thyroxine preparation of claim 9 further comprising adjuvants and auxiliary agents suitable for a composition to be administered by an transdermal administration method.

11. The pharmaceutically active thyroxine preparation of claim 10 comprising a reservoir containing a hydrogel having said thyroxin composition therein.

12. The pharmaceutically active thyroxine preparation of claim 9 further comprising at least one gelling agent selected from the group consisting of a polyacrylic acid, a polyacrylic acid derivative, and mixtures thereof.

13. A method of administering a thyroxine to a patient in need thereof, comprising administering to said patient the composition of claim 1.

14. The method of claim 13 wherein said composition is in the form of a transdermal patch.

15. The method of claim 13 wherein said composition comprises γ-cyclodextrin and a thyroxine selected from the group consisting of L-thyroxin, pharmaceutically acceptable salts of L-thyroxin, and mixtures thereof.

16. The transdermal composition of claim 1 wherein said thyroxine is a pharmaceutically acceptable alkali metal salt of D-thyroxine, a pharmaceutically acceptable alkali metal salt of L-thyroxine, or a mixture or racemate thereof.

* * * * *